(12) United States Patent
Banas et al.

(10) Patent No.: US 8,920,660 B2
(45) Date of Patent: *Dec. 30, 2014

(54) METHOD FOR MAKING GROOVES ON A LUMINAL SURFACE OF AN INTRAVASCULAR STENT

(71) Applicant: Advanced Bio Prosthetic Surfaces, Ltd., a wholly owned subsidiary of Palmaz Scientific, Inc., Dallas, TX (US)

(72) Inventors: Christopher E. Banas, Breckenridge, CO (US); Julio C. Palmaz, Napa, CA (US); Eugene A. Sprague, San Antonio, TX (US)

(73) Assignee: Advanced Bio Prosthetic Surfaces, Ltd., a wholly owned subsidiary of Palmaz Scientific Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,475

(22) Filed: Aug. 19, 2013

(65) Prior Publication Data

US 2014/0054258 A1 Feb. 27, 2014

Related U.S. Application Data

(60) Continuation of application No. 13/168,878, filed on Jun. 24, 2011, now Pat. No. 8,512,579, which is a division of application No. 09/861,219, filed on May 18, 2001, now Pat. No. 8,037,733.

(60) Provisional application No. 60/206,060, filed on May 19, 2000.

(51) Int. Cl.
*B32B 1/08* (2006.01)
*B44C 1/22* (2006.01)
*C23F 1/02* (2006.01)
*A61F 2/91* (2013.01)
*A61F 2/915* (2013.01)

(52) U.S. Cl.
CPC .......... *A61F 2/91* (2013.01); *A61F 2002/91541* (2013.01); *C23F 1/02* (2013.01); *A61F 2/915* (2013.01)
USPC ...................... 216/8; 216/48; 216/56; 216/94

(58) Field of Classification Search
None
See application file for complete search history.

(56) References Cited

U.S. PATENT DOCUMENTS

| | | | |
|---|---|---|---|
| 1,318,487 A | 10/1919 | Donaldson | 409/250 |
| 2,375,481 A | 5/1945 | Lee et al. | 29/148 |

(Continued)

FOREIGN PATENT DOCUMENTS

| | | | |
|---|---|---|---|
| EP | 0734699 | 10/1996 | A61F 2/06 |
| EP | 0850604 | 7/1998 | A61F 2/06 |

(Continued)

OTHER PUBLICATIONS

Chehroudi, et al., "Titanium-coated Micromachined Grooves of Different Dimensions Affect Epithelial and Connective-Tissue Cells Differently in vivo", Journal of Biomedical Materials Research, vol. 24(9) pp. 1203-1219 (1990).

(Continued)

*Primary Examiner* — Duy Deo
(74) *Attorney, Agent, or Firm* — David G. Rosenbaum; J. Peter Paredes; Rosenbaum IP, P.C.

(57) ABSTRACT

Methods for manufacturing intravascular stents are disclosed wherein the intravascular stent has its inner surface treated to promote the migration of endothelial cells onto the inner surface of the intravascular stent. In particular, the inner surface of the intravascular stent has at least one groove formed therein.

18 Claims, 11 Drawing Sheets

(56) References Cited

U.S. PATENT DOCUMENTS

| | | | | |
|---|---|---|---|---|
| 2,557,722 | A | 6/1951 | Brauchler | 72/353.4 |
| 2,618,182 | A | 11/1952 | Teetor | 80/5.1 |
| 3,122,830 | A | 3/1964 | Dawson et al. | 72/370.21 |
| 4,425,696 | A | 1/1984 | Torniainen | 29/157.3 |
| 4,437,327 | A | 3/1984 | Madden | 72/94 |
| 4,733,665 | A | 3/1988 | Palmaz | 128/343 |
| 5,102,417 | A | 4/1992 | Palmaz | 606/195 |
| 5,195,984 | A | 3/1993 | Schatz | 606/195 |
| 5,772,864 | A | 6/1998 | Moller et al. | 205/73 |
| 5,824,052 | A | 10/1998 | Khosravi et al. | 623/1 |
| 5,824,053 | A | 10/1998 | Khosravi et al. | 623/1 |
| 5,843,172 | A | 12/1998 | Yan | 623/1 |
| 5,855,802 | A | 1/1999 | Acciai et al. | 216/8 |
| 5,893,887 | A | 4/1999 | Jayaraman | 623/1 |
| 6,001,124 | A | 12/1999 | Bachinski | 623/1 |
| 6,007,573 | A | 12/1999 | Wallace et al. | 623/1 |
| 6,019,784 | A | 2/2000 | Hines | 623/1 |
| 6,190,404 | B1 * | 2/2001 | Palmaz et al. | 623/1.15 |
| 8,512,579 | B2 * | 8/2013 | Banas et al. | 216/8 |
| 2002/0193336 | A1 | 12/2002 | Elkins et al. | 514/44 |
| 2003/0105512 | A1 | 6/2003 | Kanesaka | 623/1.15 |
| 2011/0091515 | A1 | 4/2011 | Zilberman et al. | 424/409 |
| 2012/0223056 | A1 | 9/2012 | Banas et al. | 219/69.17 |

FOREIGN PATENT DOCUMENTS

| | | | |
|---|---|---|---|
| EP | 0974314 | 1/2000 | A61F 2/06 |
| JP | 58-188519 | 11/1983 | B21D 17/00 |
| JP | 11-042283 | 2/1999 | A61M 29/00 |
| WO | WO99-23977 | 5/1999 | A61F 2/06 |
| WO | WO99-61261 | 12/1999 | B44C 1/22 |
| WO | WO00-10623 | 3/2000 | A61L 31/14 |
| WO | WO01-00112 | 1/2001 | A61F 2/06 |

OTHER PUBLICATIONS

Hehriein, et al., Influence of Surface Texture and Charge on the Biocompatibility of Endovascular Stents, Coronary Artery Disease, vol. 6 pp. 581-586 (1995).

* cited by examiner

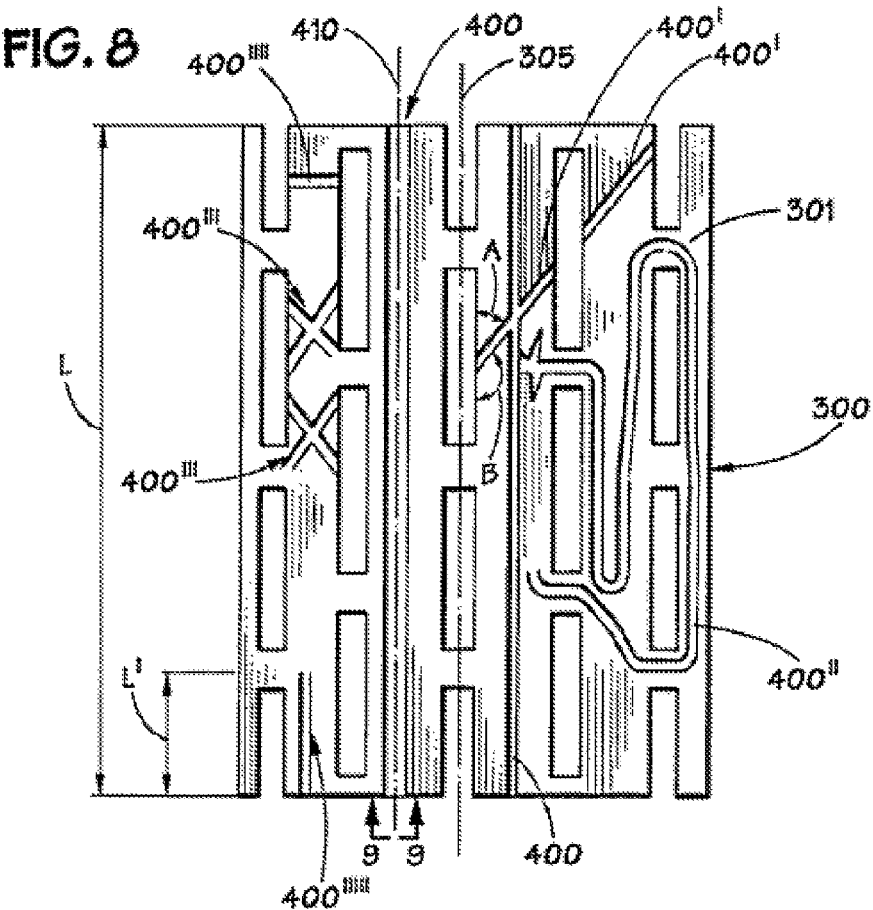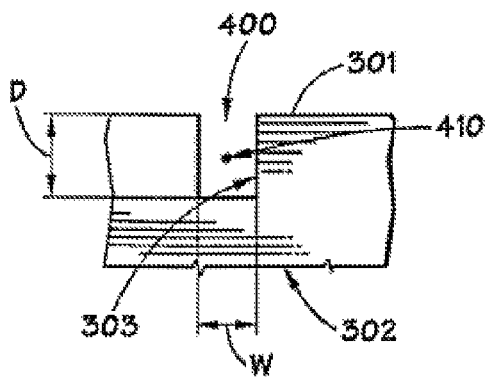

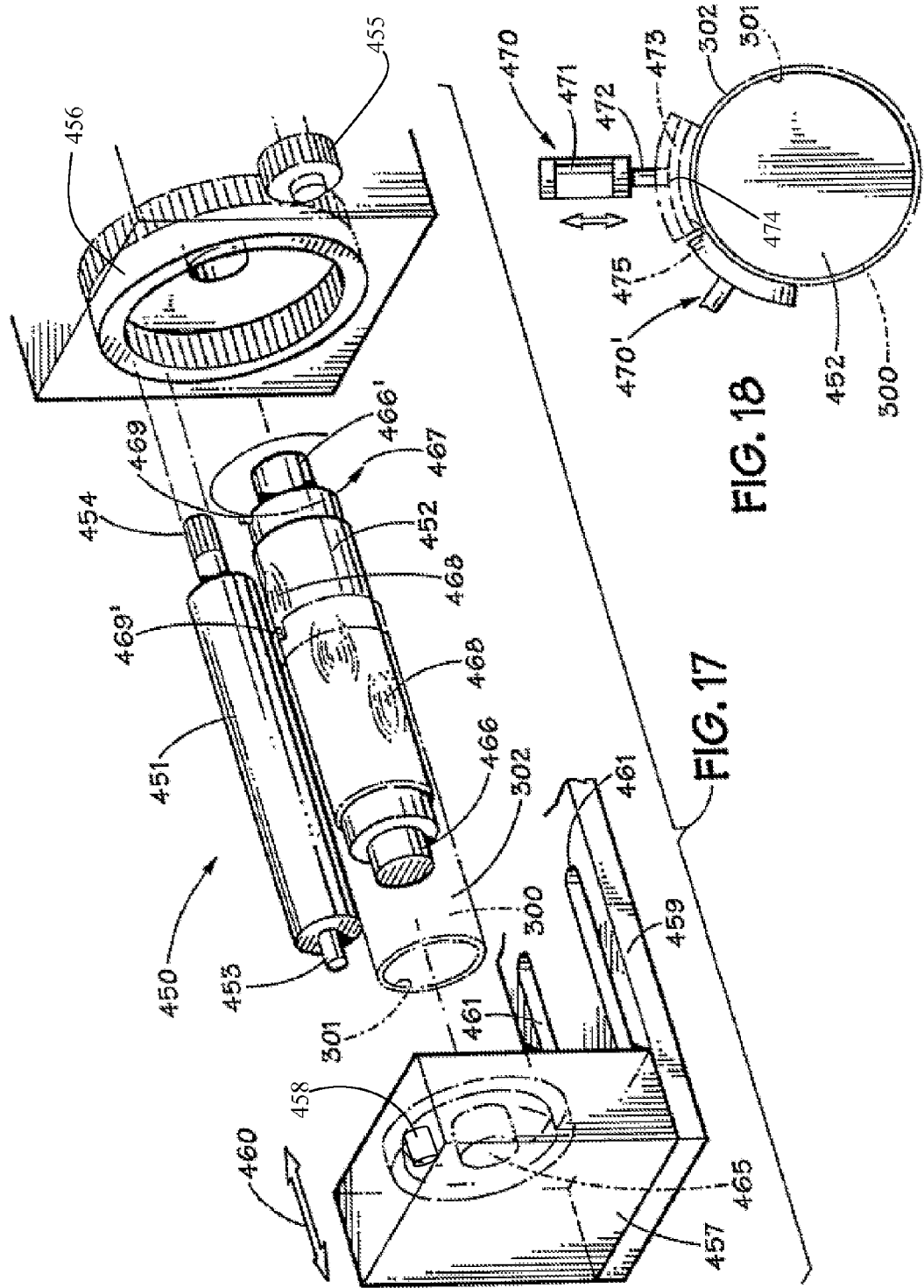

METHOD FOR MAKING GROOVES ON A LUMINAL SURFACE OF AN INTRAVASCULAR STENT

CROSS-REFERENCE TO RELATED APPLICATIONS

This is a continuation application of U.S. patent application Ser. No. 13/168,878, filed Jun. 24, 2011, which is a divisional application of commonly owned U.S. patent application Ser. No. 09/861,219, filed May 18, 2001, now U.S. Pat. No. 8,037,733, which claims priority from provisional application U.S. Provisional Application Ser. No. 60/206,060, filed May 19, 2000, all of which are incorporated by reference in their entireties.

BACKGROUND OF THE INVENTION

1. Field of the Invention

The invention relates to methods and apparatus for manufacturing intravascular stents, wherein the intravascular stent has its inner surface treated to promote the migration of endothelial cells onto the inner surface of the intravascular stent.

2. Description of Related Art

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Intravascular stents are used, in general, as a mechanical means to solve the most common problems of percutaneous balloon angioplasty, such as elastic recoil and intimal dissection. One problem intraluminal stent placement shares with other revascularization procedures, including bypass surgery and balloon angioplasty, is restenosis of the artery. An important factor contributing to this possible reocclusion at the site of stent placement is injury to, and loss of, the natural non-thrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Depending on a multitude of factors, such as activity of the fibrinolytic system, the use of anticoagulants, and the nature of the lesion substrate, the result of this process may range from a small mural to an occlusive thrombus. Secondly, loss of the endothelium at the interventional site may be critical to the development and extent of eventual intimal hyperplasia at the site. Previous studies have demonstrated that the presence of an intact endothelial layer at an injured arterial site can significantly inhibit the extent of smooth muscle cell-related intimal hyperplasia. Rapid re-endothelialization of the arterial wall, as well as endothelialization of the prosthetic surface, or inner surface of the stent, are therefore critical for the prevention of low-flow thrombosis and for continued patency. Unless endothelial cells from another source are somehow introduced and seeded at the site, coverage of an injured area of endothelium is achieved primarily, at least initially, by migration of endothelial cells from adjacent arterial areas of intact endothelium.

Although an in vitro biological coating to a stent in the form of seeded endothelial cells on metal stents has been previously proposed, there are believed to be serious logistic problems related to live-cell seeding, which may prove to be insurmountable. Thus, it would be advantageous to increase the rate at which endothelial cells from adjacent arterial areas of intact endothelium migrate upon the inner surface of the stent exposed to the flow of blood through the artery. At present, most intravascular stents are manufactured of stainless steel and such stents become embedded in the arterial wall by tissue growth weeks to months after placement. This favorable outcome occurs consistently with any stent design, provided it has a reasonably low metal surface and does not obstruct the fluid, or blood, flow through the artery. Furthermore, because of the fluid dynamics along the inner arterial walls caused by blood pumping through the arteries, along with the blood/endothelium interface itself, it has been desired that the stents have a very smooth surface to facilitate migration of endothelial cells onto the surface of the stent. In fact, it has been reported that smoothness of the stent surface after expansion is crucial to the biocompatibility of a stent, and thus, any surface topography other than smooth is not desired. Christoph Hehriein, et al., Influence of Surface Texture and Charge On the Biocompatibility of Endovascular Stents, Coronary Artery Disease, Vol. 6, pages 581-586 (1995). After the stent has been coated with serum proteins, the endothelium grows over the fibrin-coated metal surface on the inner surface of the stent until a continuous endothelial layer covers the stent surface, in days to weeks. Endothelium renders the thrombogenic metal surface protected from thrombus deposition, which is likely to form with slow or turbulent flow. At present, all intravascular stents made of stainless steel, or other alloys or metals, are provided with an extremely smooth surface finish, such as is usually obtained by electropolishing the metallic stent surfaces. Although presently known intravascular stents, specific including the Palmaz™ and Palmaz-Schatz™ balloon-expandable stents have been demonstrated to be successful in the treatment of coronary disease, as an adjunct to balloon angioplasty, intravascular stents could be even more successful and efficacious, if the rate and/or speed of endothelial cell migration onto the inner surface of the stent could be increased. It is believed that providing at least one groove disposed in the inner surface of a stent increases the rate of migration of endothelial cells upon the inner surface of the stent after it has been implanted. Accordingly, the art has sought methods and apparatus for manufacturing an intravascular stent with at least one groove disposed in the inner surface of the stent.

SUMMARY OF THE INVENTION

In accordance with the invention, the foregoing advantage has been achieved through the present methods and apparatus for manufacturing an intravascular stent with at least one groove disposed in the inner surface of the stent.

In one embodiment of the present invention, there is provided a method of manufacturing a metallic intravascular stent by first forming a stent having an inner surface and a outer surface; and then forming at least one groove in the inner surface of the stent by etching the inner surface with a mechanical process.

Various mechanical etching processes can be used. In one preferred embodiment, a mandrel is placed inside the stent, and then a mechanical force is provided to impart at least one groove formed on the outer surface of the mandrel to the inner surface of the stent. Such mechanical force may be provided by one or more calendaring rollers rotating against the outer surface of the stent, or by one or more stamping devices disposed about the outer surface of the stent. The mandrel may have an outer diameter equal to the inner diameter of the stent when the stent is expanded.

In another preferred embodiment, the mechanical etching process may comprise the steps of placing an impression roller inside the stent, and rotating the impression roller within the stent to impart at least one groove formed on the exterior of the impression roller into the inner surface of the stent.

In still another preferred embodiment, the mechanical etching process may comprise the steps of disposing the stent upon an expanding mandrel in the unexpanded configuration of the mandrel, and then expanding the mandrel outwardly to impart at least one groove on the outer surface of the mandrel to the inner surface of the stent. Particularly, the expanding mandrel may be formed of a plurality of mating and tapered segments having at least one groove on the outer surface.

In another preferred embodiment, the mechanical etching process may comprise the step of moving a tapered mandrel into and along the inner surface of the stent. During the movement, the tapered mandrel provides a cutting force, which cuts at least one groove onto the inner surface of the stent. Particularly, the stent is in an expanded configuration, and the tapered mandrel either has a plurality of cutting teeth on its outer surface, or has an outer surface with a metal cutting profile. More particularly, the cutting teeth may be abrasive particles including diamond chips and tungsten carbide chips.

In another embodiment of the present invention, there is provided a method of manufacturing a metallic intravascular stent by first forming a stent having an inner surface and an outer surface; and then forming at least one groove on the inner surface of the stent by etching the inner surface with a chemical process. Preferably, the chemical process may comprise the steps of coating the inner surface of the stent with a photosensitive material; inserting a mask into the stent; irradiating the inner surface of the stent by a light source; removing the mask from the stent; and etching light exposed areas to produce at least one groove In the inner surface of the stent. The mask may be disposed upon a deflated balloon before its insertion, and the balloon becomes expanded after the insertion. The light source may be a coaxial light source with multiple beams of light in a single plane, and may be displaced along the longitudinal axis of the stent. During the etching process, either the light source may be driven by a stepper motor for rotational movements, or the mask may be driven for rotational movements with the light source fixed.

In still another embodiment of the present invention, there is provided a method of manufacturing a metallic intravascular stent by first forming a stent having an inner surface and an outer surface; and then forming at least one groove on the inner surface of the stent by etching the inner surface with a laser.

In yet another embodiment of the present invention, there is provided a method of manufacturing a metallic intravascular stent by first forming a stent having an inner surface and an outer surface; and then forming at least one groove in the inner surface of the stent by etching the inner surface with an electric discharge machining process. The electric discharge machining process may include the steps of inserting an electric discharge machining electrode into the stent; rotating the electrode within the stent; and providing current to the electrode to cut at least one groove into the inner surface of the stent.

It is believed that the improvements in methods and apparatus for manufacturing intravascular stents of the present invention, when compared with presently known methods for manufacturing such stents, has the advantage of increasing the rate of migration of endothelial cells upon the inner surface of the intravascular stent.

BRIEF DESCRIPTION OF THE DRAWINGS

FIG. 8 is a plan view of an interior portion of an unexpanded intravascular stent in accordance with the present invention;

FIGS. 9-16 are various embodiments of an exploded view of a groove taken along line 9-9 of FIG. 8, illustrating various cross-sectional configurations and characteristics of various embodiments of grooves in accordance with the present invention;

FIG. 17 is an exploded perspective view of a calendaring apparatus for manufacturing stents in accordance with the present invention;

FIG. 18 is a partial cross-sectional view of a stamping apparatus for manufacturing stents in accordance with the present invention, looking down the longitudal axis of a mandrel;

FIG. 23A is a partial cross-sectional exploded view of a portion of FIG. 23;

FIG. 23B is a partial cross-sectional exploded view of a portion of FIG. 23;

While the invention will be described in connection with the preferred embodiment, it will be understood that it is not intended to limit the invention of that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
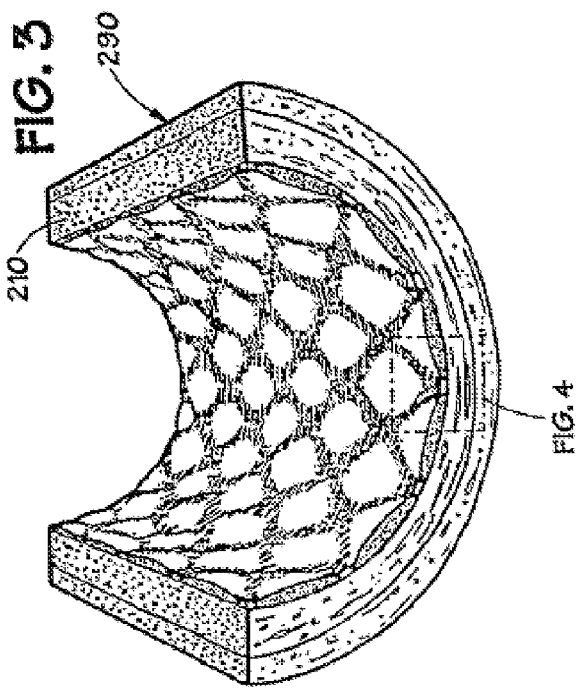
FIG. 1 is a partial cross sectional perspective view of a portion of a intravascular stent embedded within an arterial wall of a patient.
Figure 2:
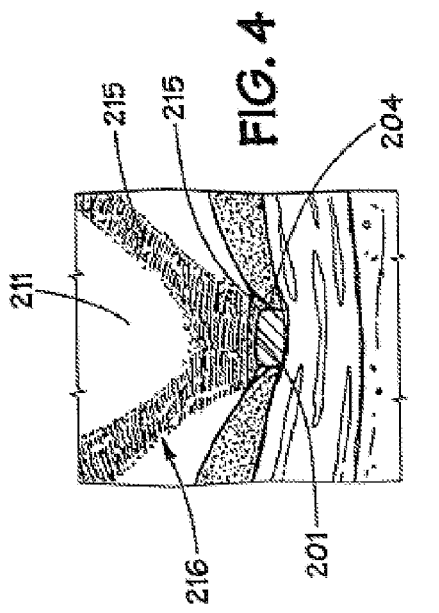
FIG. 2 is an exploded view of the outlined portion of FIG. 1 denoted as FIG. 2.

With reference to FIGS. 1 and 2, an intravascular stent 200 is illustrated being disposed within an artery 290 in engagement with arterial wall 210. For illustrative purposes only, intravascular stent 200, shown in FIGS. 1-6 is a Palmaz™ balloon-expandable stent, as is known in the art, stent 200 having an inner surface 201 and an outer surface 202. FIGS. 1 and 2 illustrate stent 200 shortly after it has been placed within artery 290, and after stent 200 has been embedded into arterial wall 210, as is known in the art. FIGS. 1 and 2 illustrate what may be generally characterized as correct placement of an intravascular stent. Stent 200 preferably includes a plurality of metal members, or struts, 203, which may be manufactured of stainless steel, or other metal materials, as is known in the art. As illustrated in FIGS. 1 and 2, correct placement of stent 200 results in tissue mounds 211 protruding between the struts 203, after struts 203 have been embedded in the arterial wall 210. Struts 203 also form troughs, or linear depressions, 204 in arterial wall 210. Dependent upon the degree of blockage of artery 290, and the type and amount of instrumentation utilized prior to placement of stent 200, the mounds of tissue 211 may retain endothelial cells (not shown).

Figure 3:
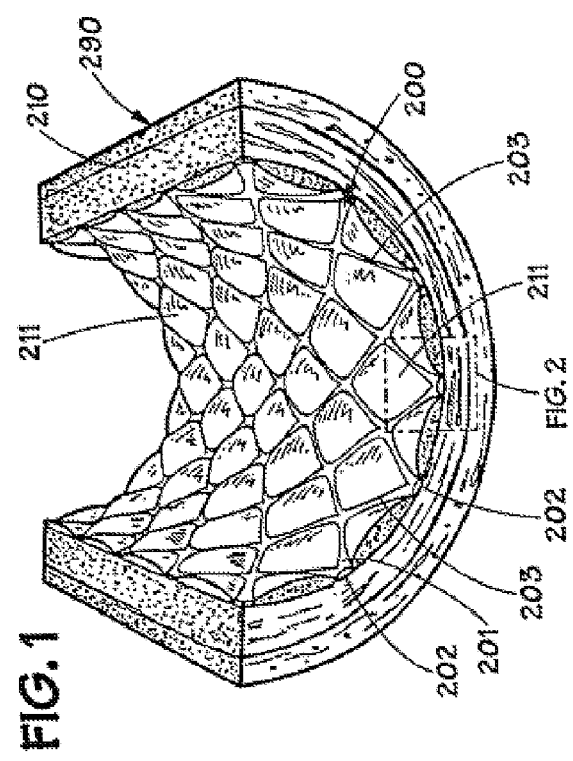
FIG. 3 is a partial cross-sectional, perspective view corresponding to FIG. 1 after the passage of time.
Figure 4:
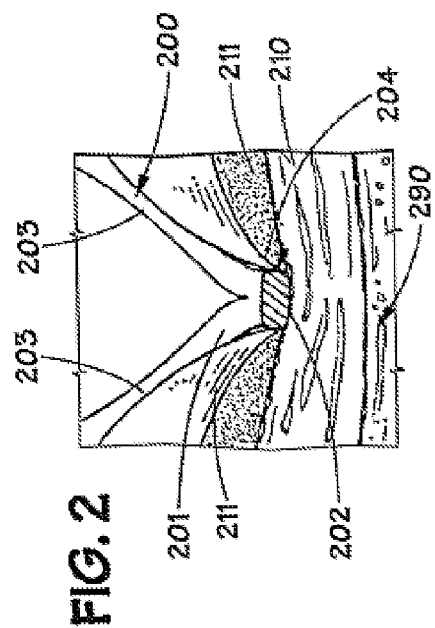
FIG. 4 is an exploded view of the outlined portion of FIG. 3 denoted as FIG. 4.

With reference to FIGS. 3 and 4, after the passage of time, a thin layer of thrombus 215 rapidly fills the depressions 204, and covers the inner surfaces 201 of stent 200. As seen in FIG. 4, the edges 216 of thrombus 215 feather toward the tissue mounds 211 protruding between the struts 203. The endothelial cells which were retained on tissue mounds 211 can provide for reendothelialization of arterial wall 210.

Figure 5:
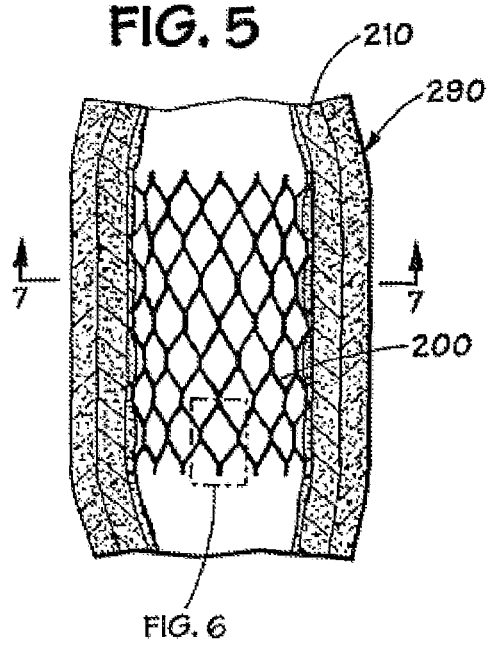
FIG. 5 is a partial cross-sectional view of the stent and artery of FIGS. 1 and 3 after a further passage of time.
Figure 6:
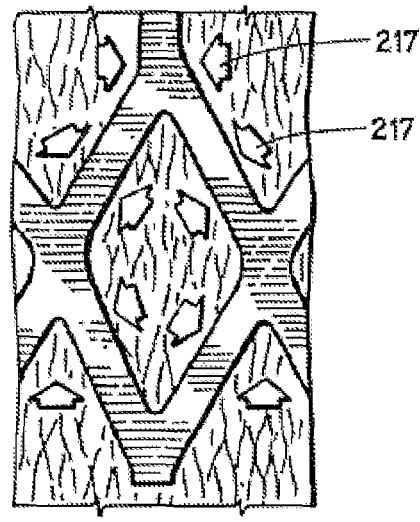
FIG. 6 is an exploded view of the outlined portion of FIG. 5 denoted as FIG. 6.
Figure 7:
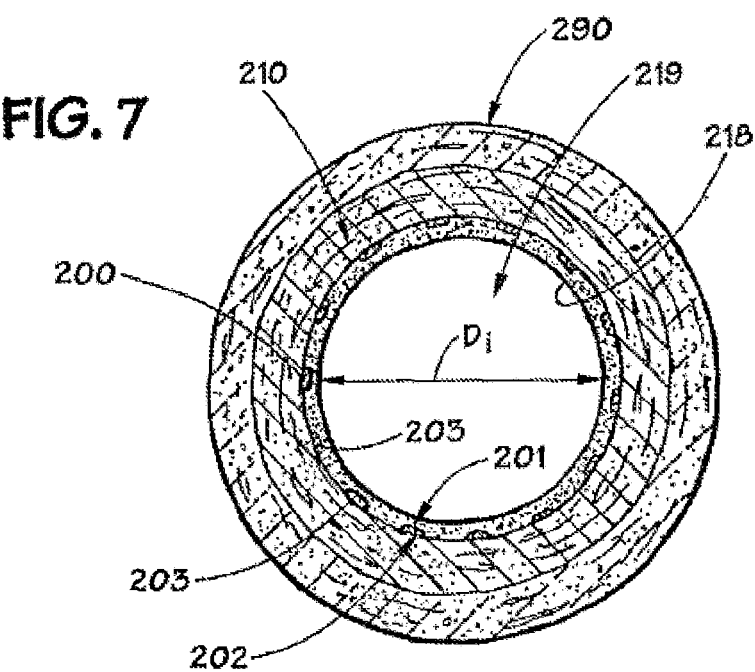
FIG. 7 is a partial cross-sectional view of the stent and artery of FIG. 5, taken along lines 7-7 of FIG. 5, and illustrates rapid endothelialization resulting in a thin neointimal layer covering the stent.
Figure 12:
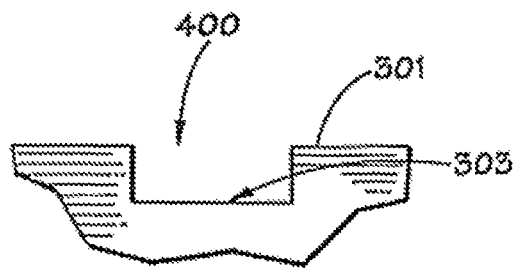

With reference to FIGS. 5 and 6, endothelial regeneration of artery wall 210 proceeds in a multicentric fashion, as illustrated by arrows 217, with the endothelial cells migrating to, and over, the struts 203 of stent 200 covered by thrombus 215. Assuming that the stent 200 has been properly implanted, or placed, as illustrated in FIGS. 1 and 2, the satisfactory, rapid endothelialization results in a thin tissue layer 218, as shown in FIG. 7. As is known in the art, to attain proper placement, or embedding, of stent 200, stent 200 must be slightly overexpanded. In the case of stent 200, which is a balloon-expandable stent, the balloon diameter chosen for the final expansion of stent 200 must be 10% to 15% larger than the matched diameter of the artery, or vessel, adjacent the site of implantation. As shown in FIG. 7, the diameter Di of the lumen 219 of artery 290 is satisfactory. If the reendothelialization of artery wall 210 is impaired by underexpansion of the stent or by excessive denudation of the arterial wall prior to, or during, stent placement, slower reendothelialization occurs. This results in increased thrombus deposition, proliferation of muscle cells, and a decreased luminal diameter Di, due to the formation of a thicker neointimal layer.

With reference to FIG. 8, an intravascular stent 300 in accordance with the present invention is illustrated. For illustrative purposes only, the structure of intravascular stent 300 is illustrated as being a PALMAZ balloon-expandable stent, as is known in the art, illustrated in its initial, unexpanded configuration. It should be understood that the improvement of the present invention is believed to be suitable for use with any intravascular stent having any construction or made of any material as will be hereinafter described. Similarly, the improvement of the present invention in methods for manufacturing intravascular stents, is also believed to be applicable to the manufacturing of any type of intravascular stent as will also be hereinafter described.

As illustrated in FIG. 8, intravascular stent, or stent, 300 has an inner surface 301, and an outer surface 302, outer surface 302 normally being embedded into arterial wall 210 in an abutting relationship. In accordance with the present invention, the inner surface 301 of stent 300 is provided with at least one groove 400. If desired, as will be hereinafter described in greater detail, a plurality of grooves 400 could be provided on, or in, inner surface 301 of stent 300. The use of the term "groove" throughout this specification and in the claims is intended to be construed as: a channel or depression; a notch or a V-shaped or rounded indentation; or a scratch, or a mark, having been made with something sharp or jagged. The at least one groove 400, or grooves, of the present invention may be provided in, or on, the inner surface 301 of stent 300 in any suitable manner, such as by: abrading the inner surface 301 of stent 300 to provide the at least one groove 400; a chemical or mechanical etching process; use of a laser or laser etching process; use of a diamond-tipped tool; use of any suitable abrasive material; or use of any tool or process, which can provide the desired groove, or grooves, 400 in, or on, the inner surface 301 of stent 300, as will be hereinafter described in greater detail.

As shown in FIG. 8, the at least one groove, or grooves, 400 may be disposed with its longitudinal axis 410 being disposed substantially parallel with the longitudinal axis 305 of stent 300. Alternatively, the longitudinal axis 410 of the at least one groove 400 may be disposed substantially perpendicular to the longitudinal axis 305 of stent 300, as illustrated by groove 400""; or the longitudinal axis 410 of the groove may be disposed at an obtuse, or acute, angle with respect to the longitudinal axis 305 of stent 300, as illustrated by groove 400'. The angle that groove 400' makes with respect to longitudinal axis 305 is either an acute or an obtuse angle dependent upon from which direction the angle is measured with respect to the longitudinal axis 305 of stent 300. For example, if the angle between the longitudinal axis of groove 400' and longitudinal axis 305 is measured as indicated by arrows A, the angle is an acute angle. If the angle is measured, as at arrows B, the angle is an obtuse angle.

Still with reference to FIG. 8, a plurality of grooves 400 may be provided on the inner surface 301 of stent 300, two grooves 400 being shown for illustrative purposes only. Instead of a plurality of individual grooves, such as grooves 400, a single groove 400" could be provided in a serpentine fashion, so as to cover as much of the inner surface 301 of stent 300 as desired. Similarly, the grooves could be provided in a cross-hatched manner, or pattern, as shown by grooves 400'". Grooves 400, 400', 400", 400'", and 400"" could be provided alone or in combination with each other, as desired, to provide whatever pattern of grooves is desired, including a symmetrical, or an asymmetrical, pattern of grooves. It should be noted that the angular disposition and location of the various grooves 400-400"" will vary and be altered upon the expansion of stent 300 within artery 201 (FIG. 1), stent 300 being illustrated in its unexpanded configuration in FIG. 8. Similarly, if stent 300 were a stent made of wire or lengths of wire, the disposition and angular orientation of the grooves formed on such wire, or wire members, would similarly be altered upon the expansion and implantation of such stent. It should be further noted, as previously discussed, that the groove, or grooves, may be provided in, or on, the inner surface of any intravascular stent, so as to increase the rate of migration of endothelial cells on, and over, the inner surface of the intravascular stent.

With reference to FIGS. 9-16, various embodiments of groove 400 will be described in greater detail. In general, as seen in FIG. 9, groove 400 has a width W, a depth D, and a length L (FIG. 8). The width W and depth D may be the same, and not vary, along the length L of the groove 400. Alternatively, the width W of the groove may vary along the length L of the groove 400. Alternatively, the depth D of the groove may vary along the length L of the at least one groove. Alternatively, both the width W and the depth D of the groove 400 may vary along the length of the at least one groove. Similarly, as with the location and angular disposition of groove, or grooves, 400 as described in connection with FIG. 8, the width W, depth D, and length L of the groove, or grooves, 400 can vary as desired, and different types and patterns of grooves 400 could be disposed on the inner surface 301 of stent 300.

Figure 13:
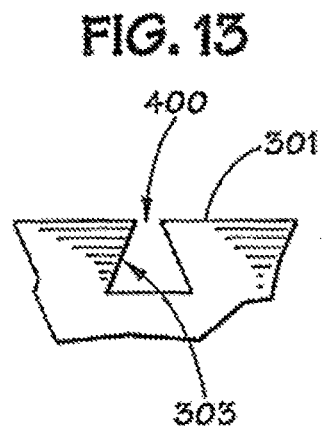
Figure 14:
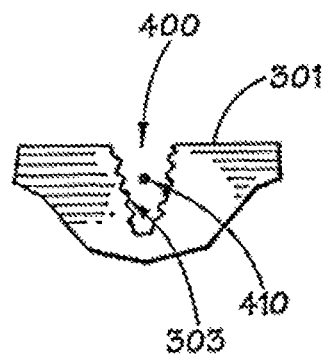
Figure 15:
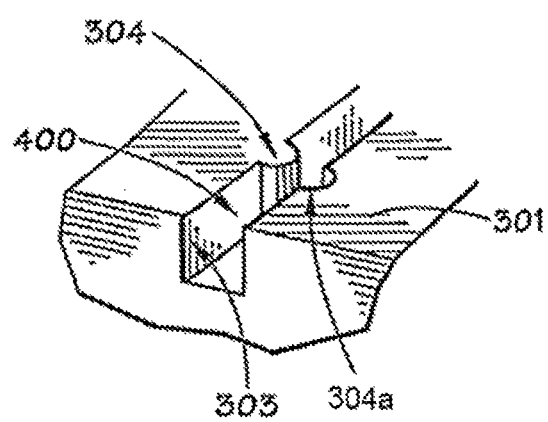
Figure 16:
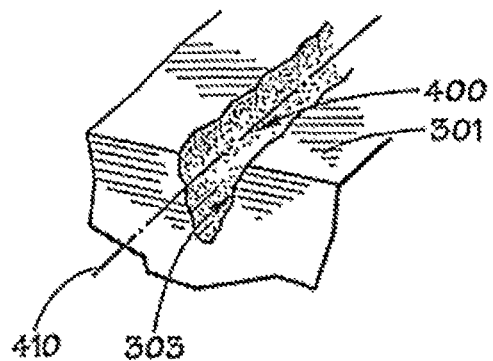

As shown in FIGS. 9-16, groove 400 may have a variety of different cross-sectional configurations. As desired, the cross-sectional configuration of the groove, or grooves, 400 may vary along the length L of the groove; or the cross-sectional configuration of the groove may not vary along the length of the at least one groove 400. Similarly, combinations of such cross-sectional configurations for the grooves could be utilized. The cross-sectional configuration of the groove, or grooves, 400 may be substantially symmetrical about the longitudinal axis 410 of groove 400 as illustrated in FIGS. 8 and 9; or the cross-sectional configuration of the at least one groove may be substantially asymmetrical about the longitudinal axis 410 of the least one groove, as illustrated in FIGS. 14 and 16. The cross-sectional configurations of groove 400 can assume a variety of shapes, some of which are illustrated in FIGS. 9-16, and include those cross-sectional configurations which are substantially: square shaped (FIG. 9); U shaped (FIG. 10); triangular, or V shaped (FIG. 1); rectangular shaped (FIG. 12); and triangular, or keyway shaped (FIG. 13). The wall surface 303 of each groove 400 may be substantially smooth, such as illustrated in FIGS. 9-13, or wall surface 303 may be jagged, or roughened, as illustrated in FIGS. 14 and 16. As illustrated in FIG. 15, wall surface 303 could also be provided with at least one protrusion 304 and at least one indentation 304a if desired, and additional protrusions and indentations 304, 304a could be provided as desired.

The depth D of groove, or grooves, 400 may fall within a range of approximately one-half to approximately ten microns. The width W of groove, or grooves, 400, may fall within a range of approximately two to approximately forty microns. Of course, the width W and depth D could be varied from the foregoing ranges, provided the rate of migration of endothelial cells onto stent 300 is not impaired. The length L of groove 400 may extend the entire length of stent 300, such as groove 400 of FIG. 8; or the length L' of a groove may be less than the entire length of stent 300, such as groove 400"" in FIG. 8. The groove, or grooves, of the present invention may be continuous, or discontinuous, along inner surface 301 of stent 300.

The portion of the inner surface 301 of stent 300 which has not been provided with a groove, or grooves, 400 in accordance with the present invention, may have any suitable, or desired, surface finish, such as an electropolished surface, as is known in the art, or may be provided with whatever surface finish or coating is desired. It is believed that when at least one groove in accordance with the present invention is disposed, or provided, on, or in, the inner surface 301 of an intravascular stent 300, after the implantation of stent 300, the rate of migration of endothelial cells upon the inner surface 301 of stent 300 will be increased over that rate of migration which would be obtained if the inner surface 301 were not provided with at least one groove in accordance with the present invention.

To manufacture intravascular stents with at least one groove disposed in the inner surface of the stent, the current best technology for inscribing microgrooves on metals seems to be photoetching. The present invention provides improved methods of inscribing the grooved pattern inside an intact tubular stent.

With reference to FIG. 17, a calendaring apparatus 450 is illustrated forming at least one groove 400 (not shown) on, or in, the inner surface 301 of stent blank 300. Calendaring apparatus 450 includes at least one calendaring roller 451 and an inner mandrel 452. Calendaring roller 451 is provided with a bearing shaft 453 and a pinion gear 454, which is driven by a gear drive 455 and gear drive apparatus 456. Bearing shaft 453 is received in a bearing block 457, which has a groove 458 for receipt of bearing shaft 453. Bearing block 457 also includes a bottom plate 459 and bearing block 457 is movable therein, in the direction shown by arrows 460, as by slidably mating with slots 461 formed in bottom plate 459. Bearing block 457 is further provided with an opening, or bearing journal, 465 for rotatably receiving mounting hub 466 disposed upon the end of mandrel 452. Calendaring roller is rotated in the direction shown by arrow 467 and bears against the outer surface 302 of stent blank 300, with a force sufficient to impart the groove pattern 468 formed on the outer surface of mandrel 452 to the inner surface 301 of stent blank 300. Mandrel 452 will have a raised groove pattern 468 on the outer surface of mandrel 452, corresponding to the desired groove, or grooves, 400 to be formed on, or in, the inner surface 301 of stent 300. The raised groove pattern 468 of mandrel 452 must be hardened sufficiently to enable the formation of many stents 300 without dulling the groove pattern 468 of mandrel 452. Mandrel 452 may have a working length corresponding to the length of the stent 300 and an overall length longer than its working length, to permit the receipt of mandrel mounting hub 466 within bearing block 457 and mounting hub 466' within gear drive apparatus 456.

Still with reference to FIG. 17, the outer diameter of mandrel 452 is preferably equal to the inner diameter of the stent 300 in its collapsed state. The groove pattern 468 may correspond to the desired groove pattern of groove, or grooves, 400 to be formed on the inner surface 301 of stent 300 after stent 300 has been fully expanded. If the desired groove pattern upon expansion of stent 300 is to have the groove, or grooves 400 become parallel to each other upon expansion of the stent 300, along the longitudal axis of the expanded stent 300, groove pattern 468, or the pre-expanded groove pattern, must have an orientation to obtain the desired post expansion groove pattern, after radial expansion of stent 300. Stent 300 may be pre-expanded slightly to facilitate its placement on the mandrel 452 in order to prevent scratching of the stent 300. Mandrel 452 may include an orientation mechanism, or pin 469 which mates with a corresponding notch 469' on stent blank 300, in order to insure proper orientation of stent blank 300 with respect to mandrel 452. Stent 300 may be crimped circumferentially around mandrel 452 after it has been properly oriented. The force to impart the desired groove pattern 468 upon, or in, the inner surface 301 of stent 300 is provided by calendaring roller 451.

With reference to FIG. 18, an alternative structure is provided to impart the desired groove pattern in, or upon, the inner surface 301 of stent blank 300. In lieu of calendaring roller 451, a punch press, or stamping apparatus, 470 may be utilized to force the inner surface 301 of stent 300 upon the groove pattern 468 of mandrel 452. Stamping apparatus 470 may include a hydraulic cylinder 471 and hydraulic piston 472, attached to a stamping segment 473. The inner surface 474 of stamping segment 473 has a radius of curvature which matches the outer radius of curvature 475 of stent 300, when it is disposed upon mandrel 452. If desired, a plurality of stamping devices 470' may be disposed about the outer surface 302 of stent 300, or alternatively a single stamping device 470 may be utilized, and stent 300 and mandrel 452 may be rotated to orient the stent 300 beneath the stamping segment 473.

Figure 19:
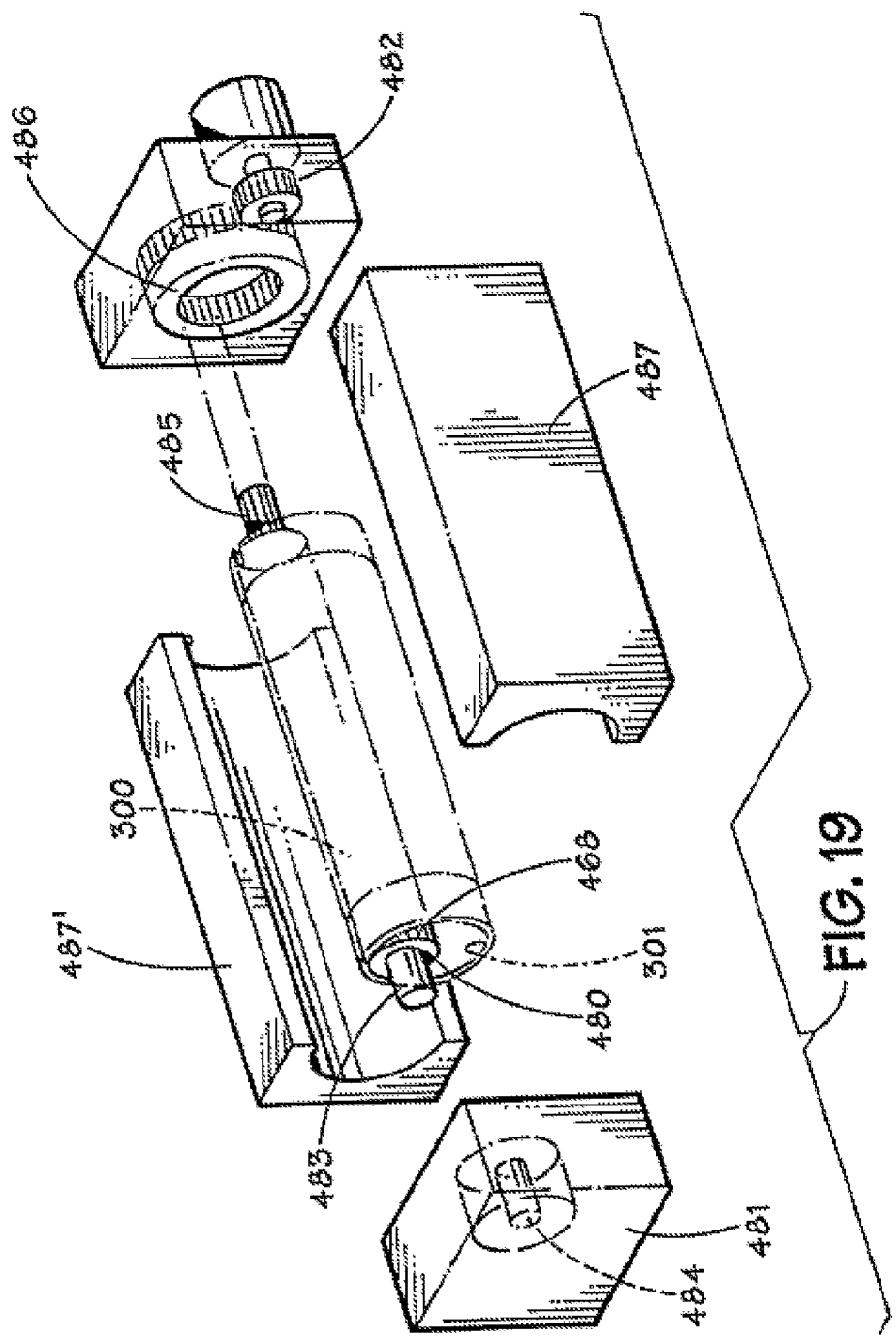
FIG. 19 is an exploded perspective view of an apparatus utilizing an impression roller to manufacturer stents in accordance with the present invention.

With reference to FIG. 19, the desired grooves 400 may be formed on the inner surface 301 of stent blank 300 by an impression roller 480 which serves as the inner mandrel. Impression roller 480 is supported at its ends by roller bearing block 481, similar in construction to previously described bearing block 457. Similarly, a gear drive, or drive gear mechanism, 482 may be provided, which is also similar in construction to gear drive 455. Impression roller 480 has a bearing shaft 483 at one end of impression roller 480, bearing shaft 483 being received by an opening, or journal bearing, 484 in bearing block 481. The other end of impression roller 480 may have a pinion gear 485 which is received within rotating ring gear 486 in gear drive mechanism 482. A backup housing, such as a two-part backup housing 487, 487' may be provided for fixedly securing stent blank 300 while impression roller 480 is rotated within stent blank 300 to impart groove pattern 468 formed on the exterior of impression roller 480 to the inner surface 301 of stent blank 300.

Figure 20:
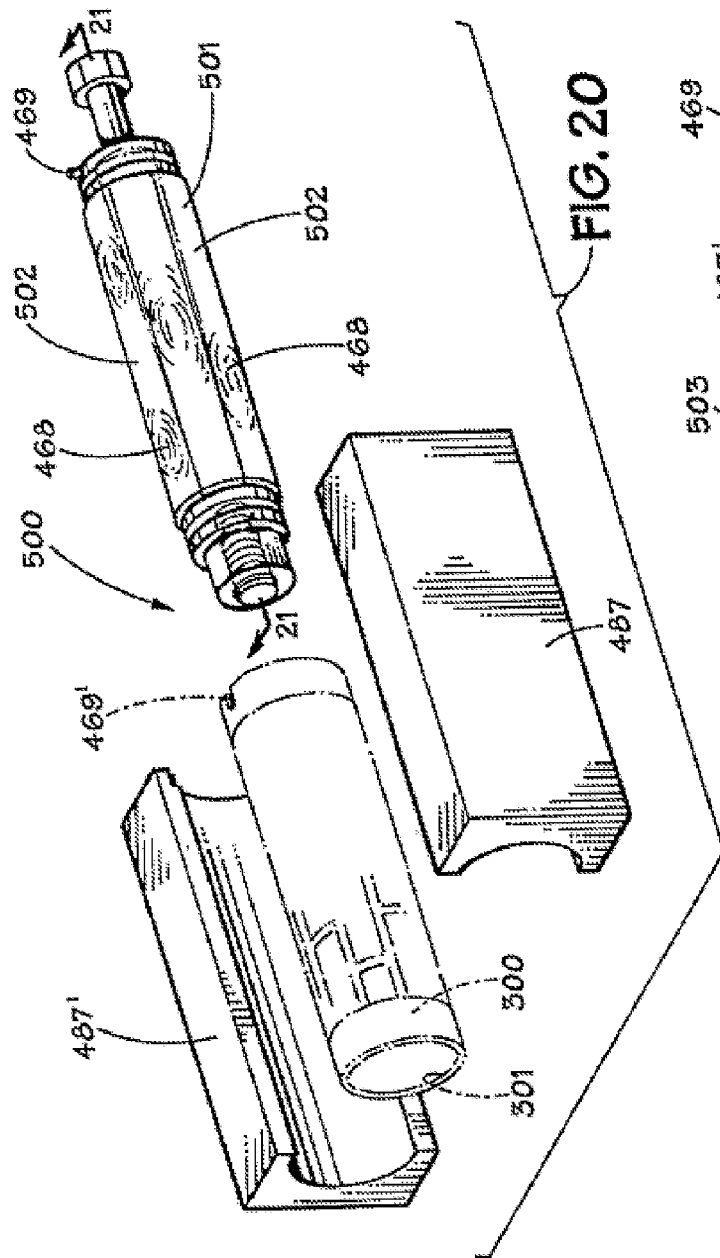
FIG. 20 is an exploded perspective view of an expanding mandrel apparatus for manufacturing stents in accordance with the present invention.
Figure 21:
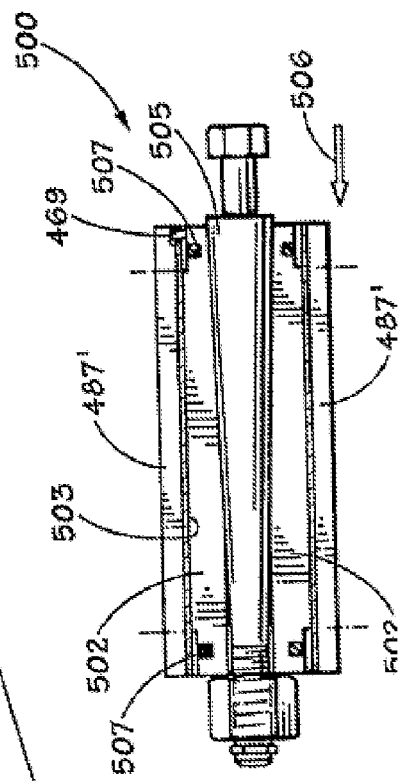
FIG. 21 is a partial cross-sectional view of the mandrel of FIG. 20, taken along lines 21-21 of FIG. 20.

With reference to FIGS. 20 and 21, an expanding mandrel apparatus 500 for forming the desired at least one groove 400 on, or in, the inner surface 301 of stent blank 300 is illustrated. Expanding mandrel 501 is preferably formed of a plurality of mating and tapered segments 502 having the desired groove pattern 468 formed on the outer surface 503 of each segment 502. Stent blank 300 is disposed upon expanding mandrel 501 in the unexpanded configuration of expanding mandrel 501, stent blank 300 being oriented with respect to mandrel 501, as by the previously described notch 469' and pin 469. A backup housing 487 and 487', as previously described in connection with FIG. 19, may be utilized to retain stent blank 300 while expanding mandrel 501 is expanded outwardly to impart the desired groove pattern 468 upon, or in, the inner surface 301 of stent blank 300. In this regard, expanding mandrel 501 is provided with a tapered interior piston 505, which upon movement in the direction of arrow 506 forces mandrel segments 502 outwardly to assume their desired expanded configuration, which forces groove pattern 468 on mandrel 501 against the inner surface 301 of stent blank 300. O-rings 507 may be utilized to secure stent 300 upon mandrel 501.

Figure 22:
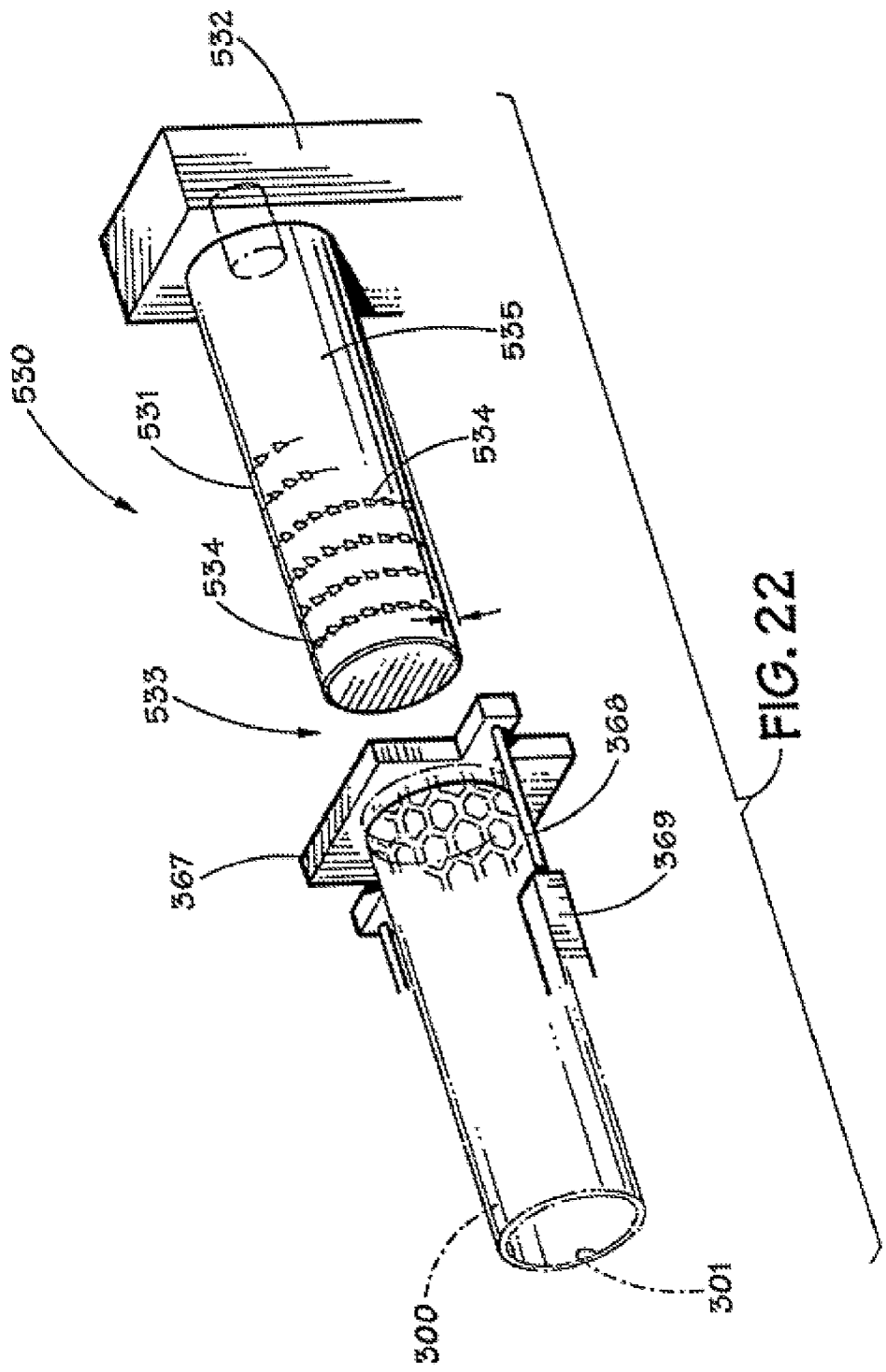
FIG. 22 is an exploded perspective view of an apparatus utilizing a tapered mandrel to manufacture stents in accordance with the present invention.

With reference to FIG. 22, a tapered mandrel groove forming apparatus 530 is illustrated. Tapered mandrel 531 is supported by a mandrel support bracket, or other suitable structure, 532 to fixedly secure tapered mandrel 531 as shown in FIG. 22. The end 533 of tapered mandrel 531, has a plurality of cutting teeth 534 disposed thereon. The cutting teeth 534 may be abrasive particles, such as diamond chips, or tungsten carbide particles or chips, which are secured to tapered mandrel 531 in any suitable manner, and the cutting teeth 534 form the desired groove, or grooves, 400 on, or in, the inner surface 301 of stent blank 300. Alternatively, instead of cutting teeth 534, the outer surface 535 of tapered mandrel 531 could be provided with a surface comparable to that formed on a metal cutting file or rasp, and the file, or rasp, profile would form the desired grooves 400. A stent holding fixture 367 is provided to support stent blank 300 in any desired manner, and the stent holding fixture 367 may be provided with a piston cylinder mechanism, 368, 369 to provide relative movement of stent 300 with respect to tapered mandrel 531. Alternatively, stent 300 can be fixed, and a suitable mechanism can be provided to move tapered mandrel 531 into and along the inner surface 301 of stent 300. Preferably, stent 300 is in its expanded configuration.

Figure 23:
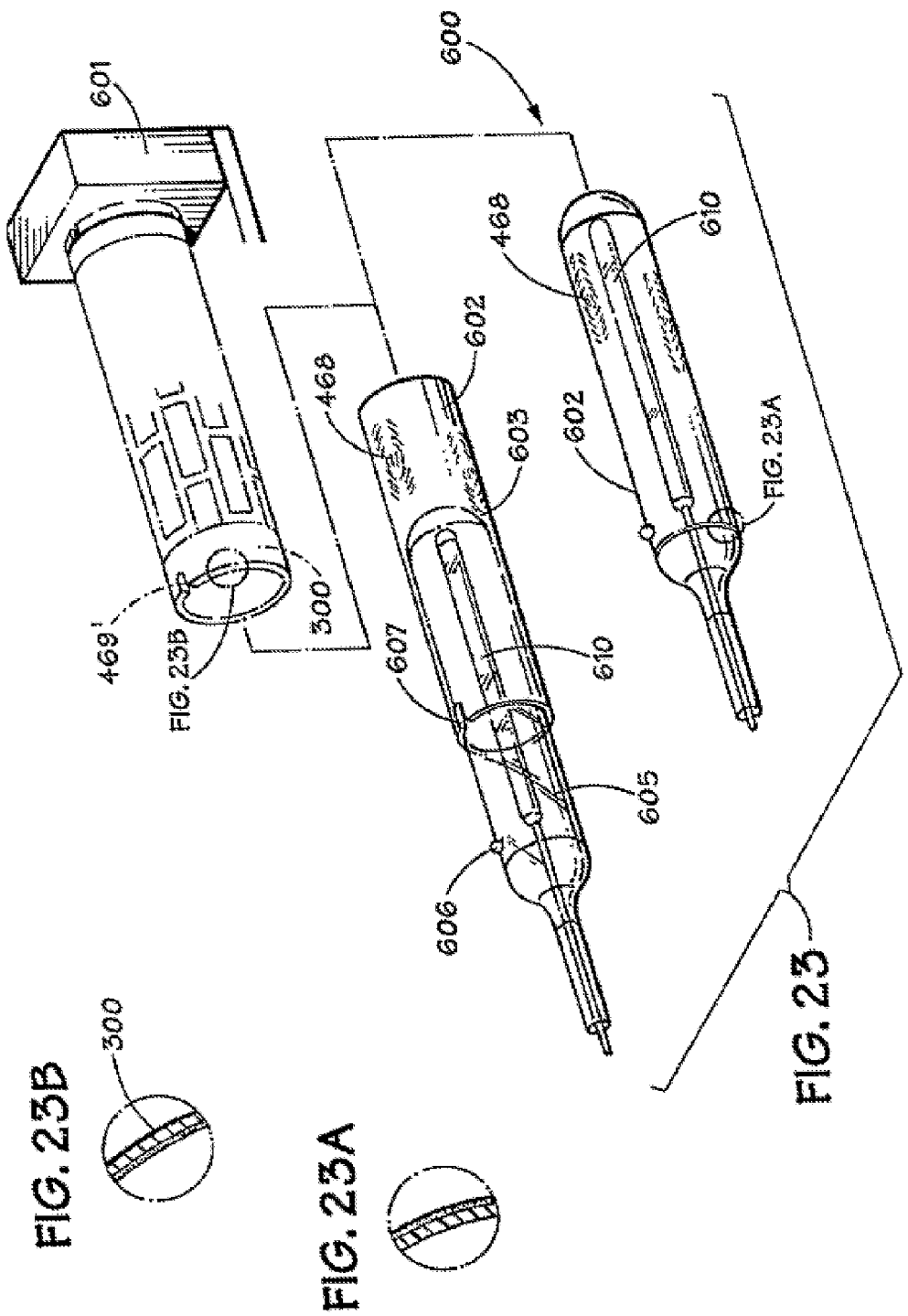
FIG. 23 is an exploded perspective view of an apparatus utilizing a chemical removal method to manufacture stents in accordance with the present invention.

With reference to FIGS. 23, 23A and 23B, a chemical removal technique and apparatus 600 for forming the desired groove, or grooves, 400 on, or in, the interior surface 301 of stent blank 300 is illustrated. A stent holding fixture 601 is provided, and holding fixture 601 may be similar in construction to that of stent holding fixture 367 of FIG. 22. Again, stent blank 300 is provided with an orientation notch, or locator slot, 469'. A photo mask 602 is formed from a material such as Mylar film. The dimensions of the mask, 602 correspond to the inner surface area of the inner surface 301 of stent 300. The mask 602 is formed into a cylindrical orientation to form a mask sleeve 603, which is wrapped onto a deflated balloon 605, such as a balloon of a conventional balloon angioplasty catheter. A conventional photoresist material is spin coated onto the inner surface 301 of stent blank 300. The mask sleeve 603, disposed upon balloon 605 is inserted into stent 300, and balloon 605 is expanded to force the mask sleeve 603 into an abutting relationship with the photoresist coated inner surface 301 of stent 300. Balloon 605 may be provided with an orientation pin 606 which corresponds with an orientation notch 607 on mask sleeve 603, which in turn is also aligned with locator slot 469' on stent blank 300. The expansion of balloon 605 is sufficient to sandwich mask sleeve 603 into abutting contact with the photoresist coated inner surface 301 of stent 300; however, the balloon 605 is not inflated enough to squeeze the photoresist material off the stent 300. The interior surface 301 of stent 300 is then irradiated through the inside of the balloon 605 through the balloon wall, as by a suitable light source 610. Balloon 605 is then deflated and mask sleeve 603 is removed from the interior of stent 300. The non-polymerized photoresist material is rinsed off and the polymerized resist material is hard baked upon the interior of stent 300. The groove, or grooves 400 are then chemically etched into the non-protected metal surface on the interior surface 301 of stent 300. The baked photoresist material is then removed by either conventional chemical or mechanical techniques.

Alternatively, instead of using a Mylar sheet as a mask 602 to form mask sleeve 603, mask 602 may be formed directly upon the outer surface of balloon 605, as shown in FIG. 23A. The production of mask 602 directly upon the balloon outer surface can be accomplished by physically adhering the mask 602 onto the outer surface of balloon 605, or by forming the mask 602 onto the surface of balloon 605 by deposition of the desired groove pattern 468 by deposition of UV absorbing material by thin film methods. In the case of utilizing mask sleeve 603 as shown in FIG. 23B, the balloon material must be compliant enough so as to prevent creases from the balloon wall which may shadow the resulting mask 602. In the case of mask 602 being formed on balloon 605 as shown in FIG. 23A, a non-compliant balloon 605 should be used, so as not to distort the resulting image by the stretching of the compliant balloon wall. If on the other hand, the mask 602 is physically adhered to the outer wall of balloon 605, a compliant balloon 605 may be used provided the mask 602 is adhered to the balloon 605 when the balloon 605 is in its fully expanded diameter.

Figure 24:
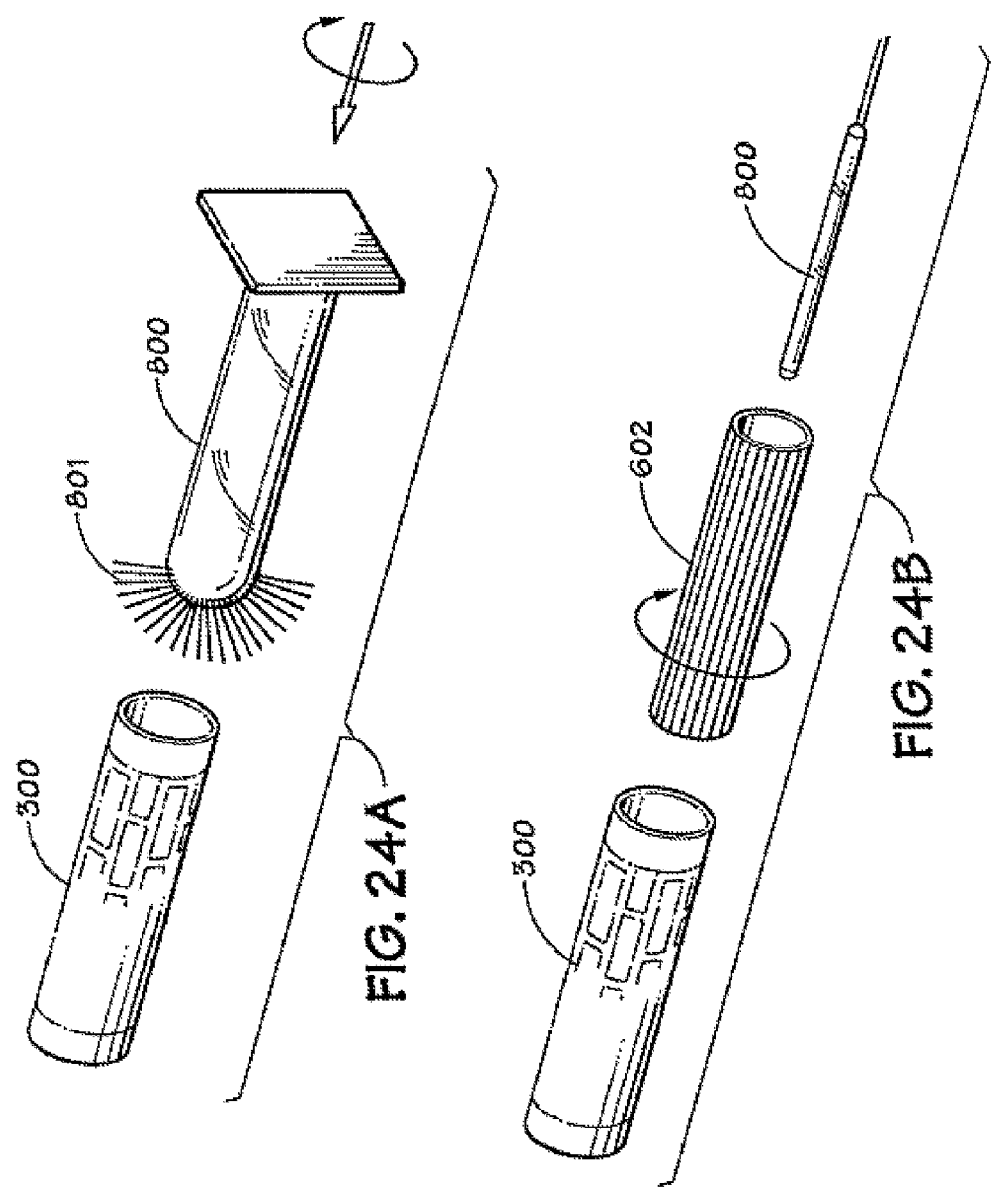
FIG. 24A is an exploded perspective view of an apparatus utilizing a rotating coaxial light source to inscribe microgrooves inside an intact tubular stent in accordance with the present invention.
FIG. 24B is an exploded perspective view of an apparatus utilizing a rotating mask and fixed light source to inscribe microgrooves inside an intact tubular stent in accordance with the present invention.

With reference to FIGS. 24A and 24B, a method is shown for creating grooves inside an intact tubular stent 300, which involves casting patterned light inside a stent 300 previously coated with photosensitive material as discussed, for example, in connection with FIG. 23 (PSM). The light exposed areas are subjected to chemical etching to produce the grooved pattern. This method involves using a coaxial light source 800 with multiple small beams 801 of light in a single plane. The light source 800 could be displaced along the longitudinal axis of the tube, or stent 300, at a rate consistent with adequate exposure of the photosensitive material. Computer driven stepper motors could be utilized to drive the light source in the x and y planes, which would allow for interlacing grooves (see FIG. 24A). One pass could create 1 mm spacing, while the next pass creates 500 µm, and so on.

Rotational movements could introduce variability in the groove direction for zig-zag, spiral or undulating patterns. Alternatively, the light source 800 could be fixed as shown in FIG. 24B, and the beams would be as narrow and long as the grooves needed on the inner surface of the mask 602. Stepping of the mask 602 would allow narrow spacing of the grooves.

Figure 25:
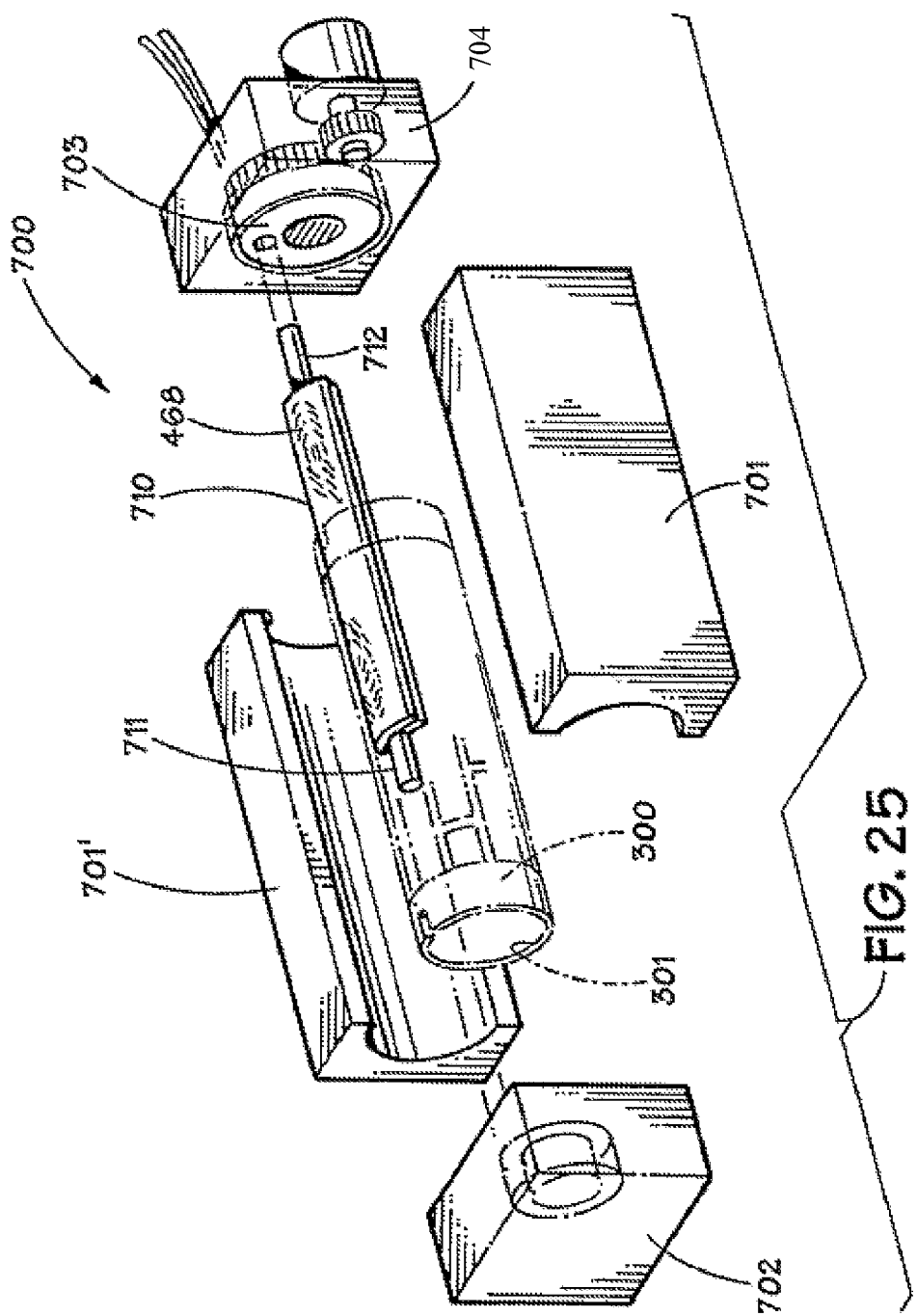
FIG. 25 is an exploded perspective view of an electric discharge machining apparatus for manufacturing stents in accordance with the present invention.

With reference to FIG. 25, an EDM process and apparatus 700 provide the desired groove, or grooves, 400 upon the interior 301 of stent 300. A non-conductive stent alignment and holding fixture 701, 701', similar in construction to backup housings 487, 487', previously described, are provided for holding stent like blank 300. A bearing block assembly 702, similar to bearing block assembly 481 of FIG. 19, is provided along with an indexing and current transfer disk 703 provided within a drive gear mechanism 704, which is similar in construction to drive gear mechanisms 482 and 455, previously described in connection with FIGS. 19 and 17. An electric discharge machining ("EDM") electrode 710 having bearing shafts 711, 712, disposed at its ends, for cooperation with bearing block assembly 702 and disk 703, respectively, is rotated within stent blank 300. Current is provided to the raised surfaces, or groove pattern, 468, of electrode 710 to cut the desired groove, or grooves 400 into the inner surface 301 of stent 300.

It is to be understood that the invention is not limited to the exact details of construction, operation, exact materials, or embodiments shown and described, as obvious modifications and equivalents will be apparent to one skilled in the art. Accordingly, the invention is therefore to be limited only by the scope of the appended claims.

What is claimed:

1. A method of manufacturing an intravascular stent comprising the steps of: providing an intravascular stent having an inner surface and an outer surface; and forming at least one groove in the inner surface of the intravascular stent by etching the inner surface by a chemical process, wherein the chemical process includes the steps of: coating the inner surface of the stent with a photosensitive material; inserting a mask into the stent; irradiating the inner surface of the stent by a light source, wherein the mask is driven for rotational movements during irradiation; removing the mask from the stent; and chemically etching the inner surface of the stent to produce at least one groove in the inner surface of the stent.

2. The method of claim 1, wherein the mask is inserted into the stent by first disposing the mask upon a deflated balloon and then inserting the deflated balloon into the stent.

3. The method of claim 2, wherein the balloon is expanded after the insertion of the balloon into the stent.

4. The method of claim 1, wherein the light source is a coaxial light source with multiple beams of light in a single plane.

5. The method of claim 1, wherein the light source is displaced along the longitudinal axis of the stent.

6. The method of claim 1, wherein the light source is driven by a stepper motor for rotational movements.

7. The method of claim 1, wherein the light source is fixed.

8. A method of manufacturing an implantable medical device, comprising the steps of: providing an implantable medical device having a first surface and a second surface, and forming at least one groove in at least one of the first surface or the second surface, the at least one groove adapted to increase the rate of endothelial cell migration upon the at least one of the first surface or the second surface, the at least one groove being formed by a chemical etching process, wherein the chemical etching process includes the steps of: coating at least one of the first surface or second surface with a photosensitive material; applying a mask to the photosensitive material; irradiating the photo sensitive material by a light source, wherein the mask is driven during irradiation; removing the mask from the photosensitive material; and chemically etching the at least one of the first surface or second surface to produce the at least one groove.

9. The method of claim 8, wherein the implantable medical device further comprises a tubular device and the method further comprises the step of inserting the mask into a lumen of the tubular device by first disposing the mask upon a deflated balloon and then inserting the deflated balloon into the lumen of the tubular device.

10. The method of claim 9, wherein the balloon is expanded after the insertion of the balloon into the lumen of the tubular device.

11. The method of claim 8, wherein the light source is a coaxial light source with multiple beams of light in a single plane.

12. The method of claim 8, wherein the light source is displaced along a longitudinal axis of the implantable medical device.

13. The method of claim 8, wherein the light source is driven by a stepper motor for rotational movements.

14. The method of claim 8, wherein the light source is fixed, while said mask is driven for rotational movements.

15. The method of claim 8, wherein the at least one groove includes a cross-sectional configurations selected from the group consisting of square shaped, U shaped, triangular, V shaped, rectangular shaped, and triangular-keyway shaped.

16. The method of claim 8, wherein the at least one groove includes a depth D within a range of approximately one-half to approximately ten microns and a width W within a range of approximately two to approximately forty microns.

17. The method of claim 1, wherein the at least one groove includes a cross-sectional configurations selected from the group consisting of square shaped, U shaped, triangular, V shaped, rectangular shaped, and triangular-keyway shaped.

18. The method of claim 1, wherein the at least one groove includes a depth D within a range of approximately one-half to approximately ten microns and a width W within a range of approximately two to approximately forty microns.

* * * * *